United States Patent

Spallek et al.

[11] Patent Number: 6,123,991
[45] Date of Patent: Sep. 26, 2000

[54] METHOD OF COATING ELASTOMERIC COMPONENTS

[75] Inventors: Michael Spallek, Ingelheim; Marten Walther, Engelstadt; Burkhard Danielzik, Ingelheim; Markus Kuhr, Saulheim, all of Germany

[73] Assignee: Schott Glas, Mainz, Germany

[21] Appl. No.: 09/205,164

[22] Filed: Dec. 4, 1998

[30] Foreign Application Priority Data

Dec. 5, 1997 [DE] Germany ............ 197 54 056

[51] Int. Cl.⁷ .................. C23C 16/00; H05H 1/24; B05D 3/12
[52] U.S. Cl. ............... 427/248.1; 427/569; 427/577; 427/578; 427/579; 427/289; 427/2.14; 427/2.28; 427/2.3
[58] Field of Search ............... 427/248.1, 569, 427/578, 579, 577, 2.28, 2.3, 575, 2.14, 289

[56] References Cited

U.S. PATENT DOCUMENTS

| | | |
|---|---|---|
| 5,064,083 | 11/1991 | Alexander et al. . |
| 5,110,621 | 5/1992 | Sudo et al. ........................ 427/2.3 |
| 5,154,943 | 10/1992 | Etzkorn et al. . |

FOREIGN PATENT DOCUMENTS

| | | |
|---|---|---|
| 0 296 878 B1 | 9/1993 | European Pat. Off. . |
| 0 497 567 B1 | 9/1996 | European Pat. Off. . |
| 38 30 249 C2 | 7/1990 | Germany . |
| 40 08 405 C1 | 7/1991 | Germany . |
| 40 34 211 C1 | 11/1991 | Germany . |
| 44 38 359 A1 | 5/1996 | Germany . |
| WO 96/34926 | 11/1996 | WIPO . |

*Primary Examiner*—Roy V. King
*Attorney, Agent, or Firm*—Michael J. Striker

[57] ABSTRACT

In order to guarantee that individual elastomeric components used for medicinal or pharmaceutical purposes have improved inertness and static and sliding friction properties, a suitable layer is provided on the elastomeric components for this purpose by the method of the invention. This method includes providing an extended flat mat made of elastomeric material including connected protruding elastomeric components; coating at least one side of the mat including the connected elastomeric components by means of a PECVD or PICVD method to provide a silicon dioxide layer containing carbon, hydrogen and/or nitrogen on the at least one side of the mat; and punching the connected elastomeric components out of the mat to form individual unconnected elastomeric components, each at least partially coated with a portion of the layer.

18 Claims, 2 Drawing Sheets

METHOD OF COATING ELASTOMERIC COMPONENTS

BACKGROUND OF THE INVENTION

1. Field of the Invention

The present invention relates to a method of coating elastomeric components for medicinal purposes.

2. Prior Art

Elastomeric components for applications, in which the pharmacological compatibility of the elastomeric components is an issue, are known in many different forms, especially as closure means for containers for food and pharmacological containers, such as injection stoppers, infusion stoppers or bottle stoppers for spraying devices. DIN ISO 11040, Part 2, requires stoppers for dental capsules made from elastomeric materials that deliver no substances that would have a deleterious effect on the therapeutic action of the injected preparation.

The specifications for rubber parts, i.e. parts which are made from an elastomeric material, in medical areas, which come into contact with aqueous solutions or suspensions during their preparation, storage and use, are generally established by the standards set forth in DIN 58 367, Part 1.

The requirements for elastomeric components or parts in similar applications are similar.

The above-described specifications can be fulfilled as much as possible by the selection of a suitable elastomeric material. Compromises must however be made to fulfill requirements for mechanical properties which is disadvantageous in many cases.

It is also known to provide the elastomeric components with an outer coating that provides the required inertness so that the other required properties of the coated elastomeric parts can be more freely selected.

Each elastomeric component is coated individually in the known methods.

A sanitary article made from rubber, especially a stopper, whose surface is laminated with a plastic film, which comprises a cyclic olefin copolymer (COC), is described in European Patent Document EP 0 497 567 B1.

European Patent Document EP 0 296 878 B1 describes a sanitary rubber object whose surface is provided with a layer of modified polysiloxane cross-linked by irradiation. This layer is applied to the object from a liquid phase.

It is comparatively expensive however to coat individual elastomeric parts. International Patent Document WO 96/349 26 describes a plasma coating process for cumulative coating of elastomeric parts, which are placed in a coating drum in which the elastomeric parts are moved. However this process guarantees no definitely uniform or complete coating on the individual elastomeric parts, since shadow or rubbing effects occur. Thus a considerable over-dimensioning of the layer must take place on average to obtain a predetermined minimum thickness of the coating on all of the parts.

Another method for cumulative coating of elastomeric components is described in U.S. Pat. No. 5,064,083. In this method the elastomeric components are placed individually in recesses or receptacles formed in a grid-like arrangement in a plate coated in certain sections with polyparaxylene. No specific results of this method are however described in this patent.

This method also is very expensive because of the individual treatment required for the individual elastomeric components, which also must be exactly aligned in the receptacles so that only the desired section will be coated.

SUMMARY OF THE INVENTION

It is an object of the present invention to provide an improved method for coating elastomeric components that does not have the above-described disadvantages.

It is also an object of the present invention to provide a method for coating of the above-described elastomeric products or components in a continuous coating process for coating from a gas phase, in which the elastomeric components are only partially coated, at least in the section or portion in which they would come into contact with the pharmaceutical solution, and in which no shadowing or rubbing effects occur.

It is another object of the present invention to provide a method of coating the elastomeric components of the above-described kind in which the resulting coating provides the elastomeric component with an improved inertness and improved sliding and static friction properties.

The method according to the invention comprises the following steps:

a) providing an extended flat mat made of elastomeric material comprising a plurality of protruding elastomeric components connected with each other;

b) coating at least one side of the mat comprising the protruding elastomeric components by means of a cold coating process, preferably by means of a PECVD process or a PICVD process, to provide a layer on the at least one side; and c) punching the connected elastomeric components, out of the mat to form individual unconnected elastomeric components each at least partially coated with a portion of the layer;

whereby the portion of the layer on each individual unconnected elastomeric component provides increased inertness and improved sliding and static friction properties to the resulting elastomeric components.

The elastomeric components can be provided with the desired coating in an economical and yet very effective manner. This layer is applied only to the location or area on the elastomeric component that comes into contact with the medicinal or pharmaceutically active solution. Because of that the amount of the input reaction or coating gas and the production time can be considerably reduced which considerably improves manufacturing costs.

According to a preferred embodiment of the invention the layer comprises a silicon dioxide layer whose properties can be influenced by building in solid layers of carbon, hydrogen and nitrogen until polymer-like properties are obtained. This type of layer guarantees the necessary inertness and the desired sliding and static friction properties of the elastomeric components. Also other layer materials that can increase its inertness can be imbedded in this base layer.

For this purpose in accordance with another preferred embodiment of the invention tetramethyldisiloxane (TMDSO), hexamethyldisiloxane (HMDSO) or a similar siloxane is used as the coating gas for the PECVD method.

Alternatively silazane can be used as the reaction gas for the PECVD process.

The PECVD process (plasma enhanced chemical vapor deposition) is described in many different literature references. Diverse products or objects are etched with very different energy supply from low frequencies (e.g. 40 kHz) to medium frequencies (e.g. 13.546 MHz) up to microwave frequencies (2.45 GHZ and more). The plasma-pulsed CVD method (PICVD) has proven to be particularly advantageous since a uniform coating can be obtained on large-surface-area substrates. Examples can be found in G. Janzen: Plazma Engineering (Plasmatechnik), Hütig Verlag, Heidelberg, 1992.

BRIEF DESCRIPTION OF THE DRAWING

The objects, features and advantages of the invention will now be illustrated in more detail with the aid of the following description of the preferred embodiments, with reference to the accompanying figures in which.

DESCRIPTION OF THE PREFERRED EMBODIMENTS

Figure 1:
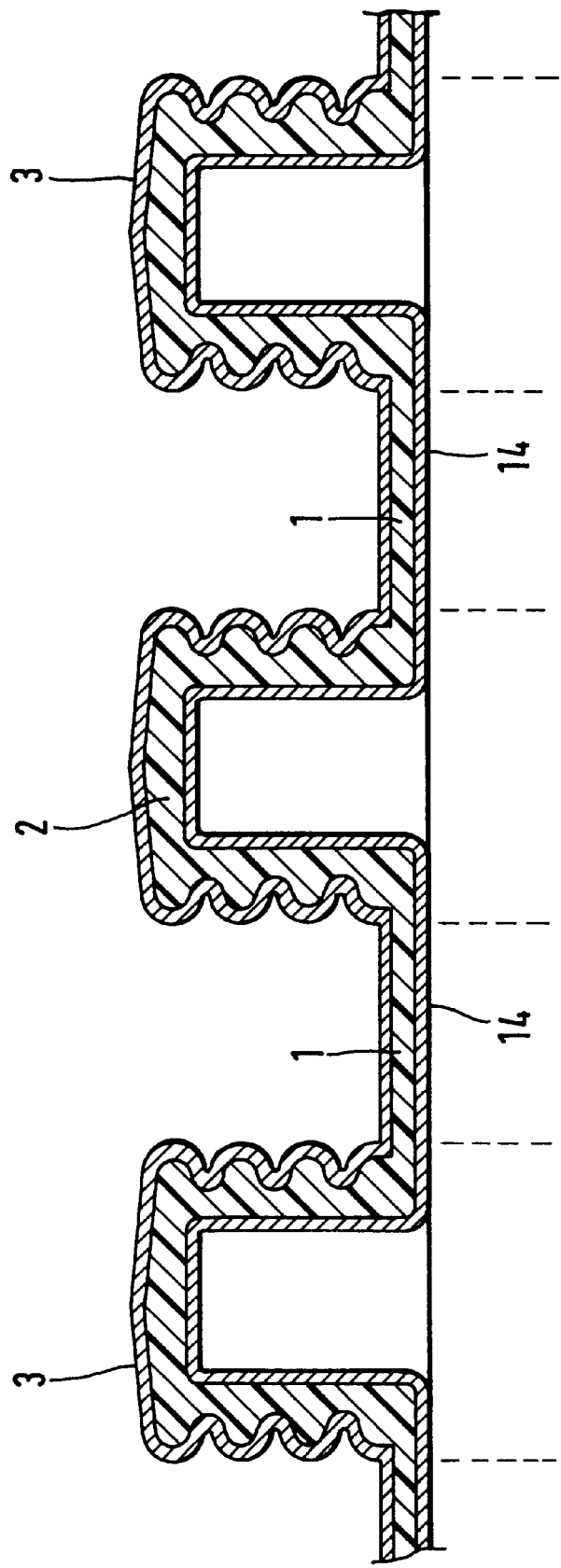
FIG. 1 is a longitudinal cross-sectional view through a coated mat comprising elastomeric parts that has been coated according to the method of the invention.

FIG. 1 shows a longitudinal cross-section through an extended flat or planar mat 1 made of the desired elastomeric material comprising the connected or molded-together elastomeric components 2. These elastomeric components 2 are stoppers in the embodiment of FIG. 1, like those of EP 0 296 878.

This mat 1 with the elastomeric components, which typically has a dimension of 30 cm, is made in the usual manner with known methods, for example by a pressing process or by an injection molding method.

In a following process the side of the mat 1 with the elastomeric components protruding upward is coated in a continuous process according to the PICVD process, and of course is provided with an upper layer 3 which improves the inertness of the elastomeric components and their static and sliding friction properties. This layer 3 is preferably a silicon dioxide layer whose properties can be influenced until they become polymer-like by building in solid layers made from carbon, hydrogen and nitrogen.

After the application of the layer, which is described in more detail hereinbelow with the aid of FIG. 2, the elastomeric components 2 are punched out from the mat 1. The punch lines are shown with dashed lines in FIG. 1.

In the embodiment shown in FIG. 1 only the top or upper side of the mat 1 is coated, i.e. the protruding surfaces of the elastomeric components 2, which come into contact with the pharmaceutical or medicinal solution in later practice. The upper side of the stopper corresponds to the bottom or under side of the mat 1, i.e. the stopper exterior during later use of the stopper as a coating element, is then not coated (other than as drawn,) so that the coating material is saved and the time for application of the layers can be reduced, since typically only the one side of the mat must be coated, not the bottom side.

The coating according the PICVD process also guarantees that no shadowing or rubbing effects occur during coating of the elastomeric components, but instead a comparatively uniform coating 3 is built up. Similarly the coating of the undercuts is guaranteed.

Figure 2:
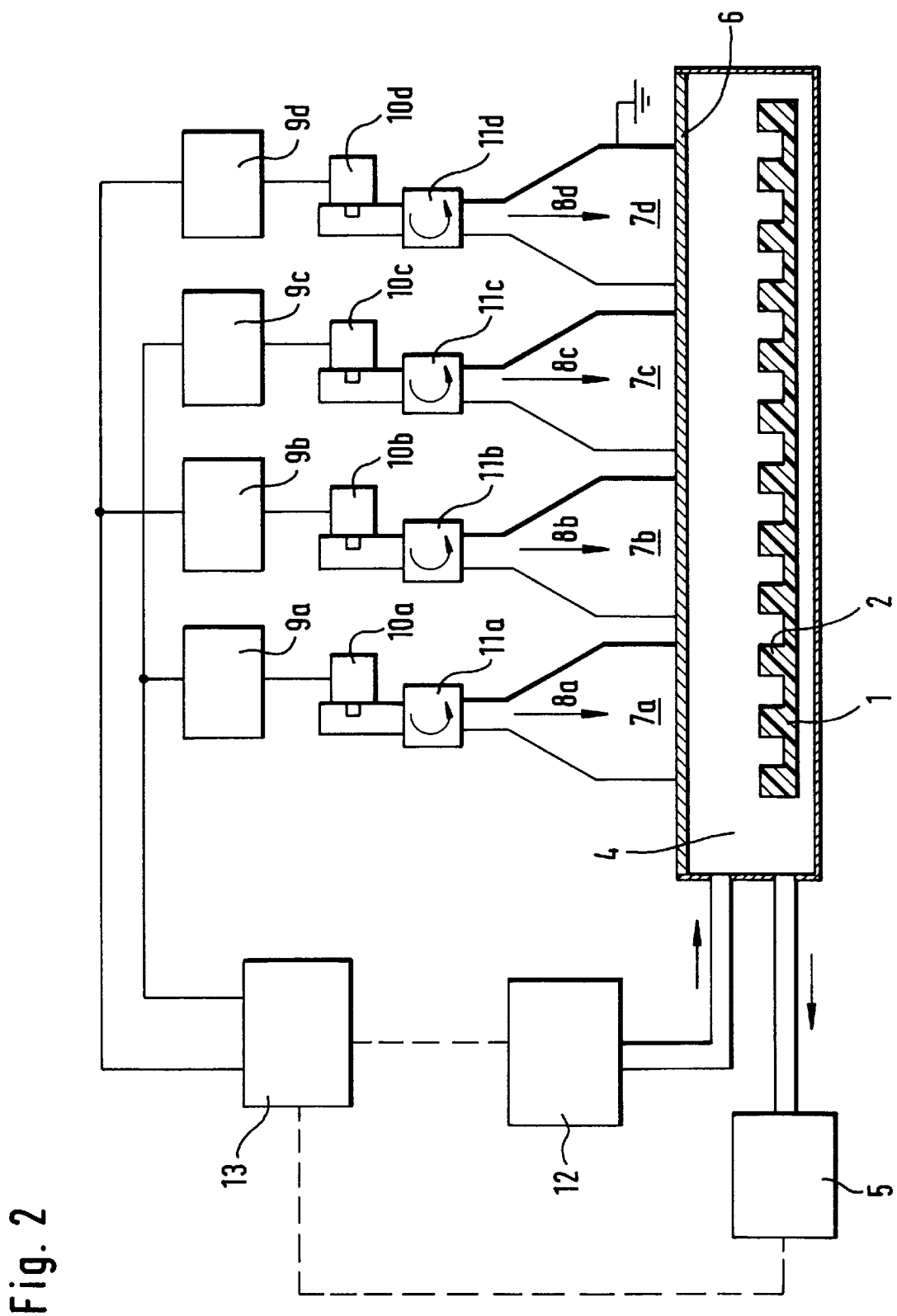
FIG. 2 is a schematic diagram of a preferred apparatus for performing the PICVD process with which the mat shown in FIG. 1 is coated.

The principle of the continuous or run-through coating station, in which the PICVD process is performed, is illustrated in FIG. 2. The mat 1 to be coated is continuously guided through a vacuum chamber 4. This vacuum chamber 4, which serves as a reaction chamber, can be evacuated by means of a vacuum device 5, which typically comprises a vacuum pump and the required valves and/or fittings, for example to a pressure of 0.3 mbar. A series of horn microwave antennae 7a to 7b, which form a linear plasma source, are arranged above the vacuum chamber 4, separated from it by a microwave window 6. Microwave radiation 8a to 8d is fed pulse-wise into the vacuum chamber 4 by means of these microwave antennae. This microwave radiation 8a to 8d forms a microwave plasma in the interior of the vacuum chamber. The pulse duration is an additional parameter, which influences the build-up of the deposited layer.

The microwave pulses, whose pulse duration is in the vicinity of from 0.1 to 10 ms, are produced by the microwave generators 9a to 9d, which are connected by means of a magnetron 10a to 10d and input guide 11a to 11d with the microwave antennae 7a to 7d. The microwave apparatus typically has standardized parts suitable for 2.45 GHz technology.

The gas, in which the plasma is ignited, which is typically oxygen and the reaction gas that is required for the coating formation, is suddenly supplied by means of the gas feed apparatus 12. The reaction gas typically can include siloxanes in the present embodiment, preferably tetramethyldisiloxane, or hexamethyldisiloxane or silazane, from which the layer 3 comprising $SiC_xH_yO_z$ is built up by selection of a suitable pulse duration.

The properties of the layer substantially depend on the parameters pulse duration and concentration of the reaction gas. Generally harder layers are deposited with smaller concentrations and longer pulse duration, which cause an increase in inertness. Softer layers with improved sliding friction properties are deposited at high concentrations and small pulse durations.

A process controller 13 controls the operation in a known manner. First the mixture of oxygen and the reaction gas is conducted into the vacuum chamber 4 by the gas feed apparatus 12. After that a plasma which cracks the molecules of the reaction gas is ignited in the vacuum chamber 4 by microwave pulses 8a to 8d. The cracking products diffuse to the adjacent surfaces, here the mat 1 with the elastomeric component 2 and gradually form a portion of the desired layer 3. In the time interval between the above-mentioned microwave pulses and the next pulses, which is from about 10 to 100 ms, the consumed reaction gas is removed from the vacuum chamber by evacuating by means of the vacuum stage 5 which has a two-stroke type motor and is replaced by fresh reaction gas and oxygen.

A multilayer coating can also be formed. Also as soon as the sufficient thickness for the first layer is reached, the associated reaction gas can be replaced by the required reaction gas for the second layer. A mixture of both reaction gases can also be supplied for a predetermined time interval to provide a gradual transition between the two types of layers. For a smooth transition the proportion of the first reaction gas can be gradually reduced and the proportion of the second reaction gas can be gradually increased at the same time to its nominal value.

The PICVD technology (Plasma Impulse Chemical Vapor Deposition) shown in FIG. 2 is known, for example, from German Patent Document DE 40 08 405 C1 and has been used for a long time for production of barrier layers in plastic containers (DE 44 38 359 A1).

The basic linear plasma source according to FIG. 2 is described in German Patent Document 38 30 249 C2. The control of the individual microwave antennae 8a to 8d occurs simultaneously in parallel or by time-delayed operation of two adjacent microwave antennae, for example according to DE 40 34 211.

After the coating the mat 1 is removed from the vacuum chamber and supplied to a further device, in which the elastomeric components are punched out of the mat, which occurs according to known engineering methods.

If increased barrier or blocking properties are desired or if transport properties should be improved, the rear side of the mat 1 according to FIG. 1 (as currently drawn in FIG. 1) may also be provided with a barrier layer 14. Different properties can be provided on the front and rear side of the mat by selection of the layer type. Suitable units, with which two layers can be simultaneously deposited on opposite sides of the mat, are known.

The disclosure in German Patent Application 197 54 056.2-45 of Dec. 5, 1997 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a method of making elastomeric components, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

We claim:

1. A method of coating elastomeric components, said method comprising the steps of:
    a) providing an extended flat mat comprising a plurality of protruding elastomeric components connected with each other in said mat;
    b) coating at least one side of the mat comprising the protruding elastomeric components to provide a layer on the at least one side of the mat; and
    c) after the coating of step b), punching the protruding elastomeric components out of the mat to form a plurality of unconnected elastomeric components, each at least partially coated with a portion of said layer;
    whereby said portion of said layer on each of said unconnected elastomeric components provides the unconnected elastomeric components with increased inertness and improved sliding and static friction properties.

2. The method as defined in claim 1, wherein said coating process is a continuous plasma-assisted CVD (PECVD) process.

3. The method as defined in claim 2, wherein said layer is a silicon dioxide layer containing carbon, hydrogen and/or nitrogen.

4. The method as defined in claim 3, further comprising supplying a reaction gas for said continuous plasma-assisted CVD process and wherein said reaction gas is a siloxane.

5. The method as defined in claim 4, wherein said siloxane is tetramethyldisiloxane (TMDSO) or hexamethyldisiloxane (HMDSO).

6. The method as defined in claim 3, further comprising supplying a reaction gas for said continuous plasma-assisted CVD process and wherein said reaction gas is silazane.

7. The method as defined in claim 1, wherein said coating process is a plasma-pulsed CVD (PICVD) process.

8. The method as defined in claim 7, wherein said layer is a silicon dioxide layer containing carbon, hydrogen and/or nitrogen.

9. The method as defined in claim 8, further comprising supplying a reaction gas for said plasma-pulsed CVD process and wherein said reaction gas is a siloxane.

10. The method as defined in claim 9, wherein said siloxane is tetramethyldisiloxane (TMDSO) or hexamethyldisiloxane (HMDSO).

11. The method as defined in claim 8, further comprising supplying a reaction gas for said plasma-pulsed CVD process and wherein said reaction gas is silazane.

12. The method as defined in claim 1, wherein said individual unconnected elastomeric components are injection stoppers, infusion stoppers or spray bottle stoppers.

13. The method as defined in claim 1, wherein said at least one side of said mat consists of a first side and said layer is provided on said first side, and further comprising providing another layer on a second side of said mat opposite from said first side.

14. The method as defined in claim 13, wherein said layer provided on said first side and said another layer provided on said second side are of different types or have different compositions.

15. A method of coating elastomeric components, said method comprising the steps of:
    a) providing an extended flat mat comprising a plurality of protruding elastomeric components connected with each other in said mat;
    b) coating at least one side of the mat comprising the protruding elastomeric components by means of a continuous plasma-assisted CVD or a plasma-pulsed CVD process to provide a silicon dioxide layer containing carbon, hydrogen and/or nitrogen on said at least one side of the mat;
    c) after the coating of step b), punching the protruding elastomeric components out of the mat to form a plurality of unconnected coated elastomeric components, each at least partially coated with a portion of said silicon dioxide layer;
    whereby said portion of said silicon dioxide layer on each of said unconnected coated elastomeric components provides increased inertness and improved sliding and static friction properties.

16. The method as defined in claim 15, wherein said continuous plasma-assisted CVD or a plasma-pulsed CVD process comprise forming a microwave plasma in a vacuum chamber in the presence of the flat mat comprising the protruding elastomeric components and feeding a mixture of oxygen and a reaction gas into said microwave plasma.

17. The method as defined in claim 16, wherein said reaction gas is a siloxane or a silazane.

18. The method as defined in claim 17, wherein said siloxane is tetramethyidisiloxane or hexamethyldisiloxane.

* * * * *